United States Patent
Chase et al.

(10) Patent No.: US 7,589,226 B2
(45) Date of Patent: Sep. 15, 2009

(54) HYDROXYALKYLDITHIOCARBAMATE ESTERS

(75) Inventors: Kevin J. Chase, Branford, CT (US); Ronald Tepper, Fairfield, CT (US)

(73) Assignee: R.T. Vanderbilt Company, Inc., Norwalk, CT (US)

( * ) Notice: Subject to any disclaimer, the term of this patent is extended or adjusted under 35 U.S.C. 154(b) by 484 days.

(21) Appl. No.: 11/255,730

(22) Filed: Oct. 21, 2005

(65) Prior Publication Data
US 2006/0106243 A1    May 18, 2006

Related U.S. Application Data

(60) Provisional application No. 60/620,978, filed on Oct. 21, 2004.

(51) Int. Cl.
*C07C 333/04* (2006.01)
(52) U.S. Cl. .................. 558/236; 558/235; 558/232
(58) Field of Classification Search ............ 558/232, 558/235, 236
See application file for complete search history.

(56) References Cited

U.S. PATENT DOCUMENTS

| | | | |
|---|---|---|---|
| 905,649 A | 12/1908 | Chapman | |
| 2,234,581 A | 3/1941 | Rosen | |
| 3,185,644 A | 5/1965 | Knowles | |
| 3,224,971 A | 12/1965 | Knowles | |
| 3,239,643 A | 3/1966 | Kluck | |
| 3,303,130 A | 2/1967 | Scypinski | |
| 3,407,222 A * | 10/1968 | Lies | 558/236 |
| 4,885,365 A * | 12/1989 | Lam | 544/161 |
| 4,997,969 A * | 3/1991 | Luciani | 558/240 |
| 5,126,063 A | 6/1992 | Cardis et al. | 252/46.3 |
| 5,182,036 A | 1/1993 | Okorodudu et al. | 252/47.5 |
| 5,370,806 A | 12/1994 | Cardis et al. | 252/46.3 |
| 5,672,727 A | 9/1997 | Chiu | 558/236 |
| 5,698,498 A * | 12/1997 | Luciani et al. | 508/193 |
| 5,698,499 A | 12/1997 | Baranski et al. | 508/198 |
| 5,885,943 A | 3/1999 | Watts et al. | 508/197 |
| 6,028,210 A | 2/2000 | Watts et al. | 558/287 |

* cited by examiner

*Primary Examiner*—Kamal A Saeed
*Assistant Examiner*—Valerie Rodriguez-Garcia

(57) ABSTRACT

A novel hydroxyalkyldithiocarbamate borate ester compound is presented according to the formula:

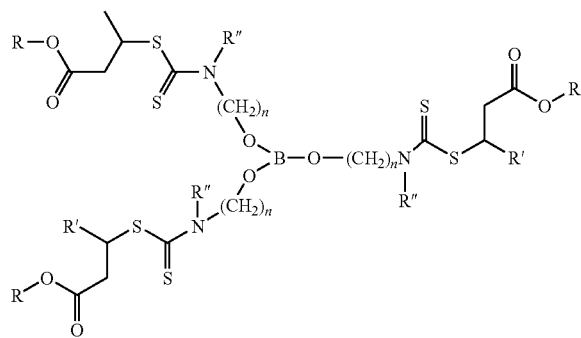

where R=alkyl $C_1$ to $C_{25}$; R'=H or $CO_2R$; R"=$(CH_2)_m$OH where m=1 to 8, or alkyl $C_1$ to $C_{25}$; n=1 to 8. The borate ester compound is prepared by reacting boric acid with a novel hydroxyalkyldithiocarbamate ester compound according to the formula, and optionally with an alcohol:

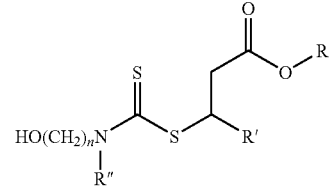

where R, R', R" and n are as above. The hydroxyalkyldithiocarbamate ester is prepared by reacting a hydroxyalkylamine with $CS_2$, and an acrylate or maleate compound. A lubricating composition is based on a major amount of lubricating oil and a minor amount of the hydroxyalkyldithiocarbamate borate ester.

8 Claims, No Drawings

HYDROXYALKYLDITHIOCARBAMATE ESTERS

BACKGROUND OF THE INVENTION

1. Field of the Invention

The invention relates to multifunctional lubricant additives for imparting antiwear and extreme pressure properties. In particular, the invention relates to novel hydroxyalkyldithiocarbamate borate esters and the process for preparing such compounds, as well as the precursor compounds and lubricating compositions containing such compounds.

2. Description of the Prior Art

The development of lubricants represents an important area of technology aimed at finding ways to reduce friction between contacted moving components in various mechanical devices. The mechanical wear of these components is greatly accelerated by friction, thus increasing the expense of operating mechanical devices.

A variety of additives are used in lubricants to substantially improve performance. For example, extreme pressure (EP) additives are routinely incorporated into an untreated lubricating composition (e.g., greases) to significantly improve performance. Extreme pressure additives are believed to produce a film on the surface of the metal which can both increase the load carrying capacity of the lubricant, and protects the metal surface under high load conditions from deterioration due to wear, welding, and abrasion.

Lead naphthenates and lead dialkyldithiocarbamates are frequently used as additives to improve the EP performance of greases. However, lead is a heavy metal which is considered "poisonous" in all forms. As an alternative, metal additives (such as antimony, zinc, and bismuth) have been used as a replacement for lead. However, these heavy metals still provide environmental concerns regarding the use. Accordingly, it has long been a goal in the art to develop non-metal lubricating materials to replace heavy metal additives while providing acceptable extreme pressure performance.

Ashless dithiocarbamates, such as 4,4'-methylene bis (dibutyl dithiocarbamate) (Trade mark VANLUBE® 7723 available from R.T. Vanderbilt Company, Inc.), are also well known for their antioxidant and extreme pressure properties in lubricants.

Borates and borate esters are well-known to exhibit antiwear and other properties in lubricant applications. U.S. Pat. No. 905,649 from Chapman describes the use of borax in a grease composition. U.S. Pat. No. 2,234,581 from Rosen describes lubricating oils and greases containing a boron-containing compound useful in lubricants. U.S. Pat. No. 3,185,644 from Knowles, et al., describes amine salts of borate esters that are useful as lubricant additives. U.S. Pat. Nos. 3,224,971 and 3,239,643, also attributed to Knowles, et al., describes novel borate esters and lubricant compositions thereof. More recently, U.S. Pat. No. 5,698,499 from Baranski, et. al., describes phenolic borates that are useful antiwear additives.

More recently, there have been reported multifunctional additives that combine both the antiwear capabilities of borates and borate esters with the extreme pressure and antioxidant properties found in ashless sulfur-containing compounds. U.S. Pat. Nos. 3,303,130, 5,885,943 and 6,028,210 describe the preparation of borate thioesters useful as antiwear additives and antioxidants. U.S. Pat. Nos. 5,126,063, 5,182,036, 5,370,806, and 5,698,498 describe the preparation of borated dithiocarbamate esters that are useful as antiwear, extreme pressure and antioxidant additives. These materials are prepared from dithiocarbamate salts and their reaction with and epoxide compound, followed by reaction with boric acid to form the borated dithiocarbamate ester. A borated dithiocarbamate is described by Chiu in U.S. Pat. No. 5,672,727.

SUMMARY OF THE INVENTION

The present invention describes the preparation of novel hydroxyalkyldithiocarbamate borate ester compounds and their novel precursors that are useful as antiwear and extreme pressure additives. This is accomplished by the reaction of a hydroxyalkylamine compound with carbon disulfide and an acrylate or maleate compound, followed by the reaction with boric acid.

The invention also relates to novel hydroxyalkyldithiocarbamate borate ester compounds formed from the reaction products of the novel hydroxyalkyldithiocarbamate ester compounds with boric acid and alcohols or glycols to form novel hydroxyalkyldithiocarbamate borate esters which provide from 0.5 to 5% B and 0.5 to 30% S by weight.

Another object of this invention concerns lubricating compositions comprising a major portion of a lubricating oil or grease and the hydroxyalkyldithiocarbamate borate ester compounds prepared herein.

DETAILED DESCRIPTION OF THE INVENTION

Hydroxyalkyldithiocarbamate Esters

Some of the hydroxyalkyldithiocarbamate esters used in this invention are the reaction products of hydroxylalkylamines and carbon disulfide with acrylates or maleates as described in Scheme I. The hydroxyalkylamine and acrylate or maleate is added to a reaction flask and carbon disulfide is then added slowly. The reaction is then heated carefully to a temperature between 60 and 120° C. for a period between 1 and 8 hours. Occasionally, a solvent such as isopropanol is used. After the period of reaction, the excess carbon disulfide and solvent is stripped, yielding the product.

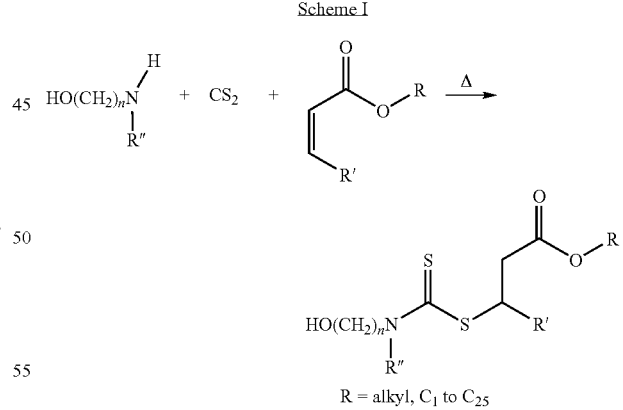

Examples of hydroxyalkylamines that can be used in this invention include ethanolamine, diethanolamine, 2-(methylamino)ethanol, 2-(ethylamino)ethanol, 2-(propylamino) ethanol, 2-(butylamino)ethanol, 2-(tertbutylamino)ethanol, 2-(isopropylamino)ethanol, 2-(propylamino)ethanol, diisopropanolamine, 2-(diisopropylamino)ethanol, 3-Methylamino-1,2-propanediol, and 3-[(2-hydroxyethyl)amino]-1-propanol. The preferred hydroxyalkylamines are diethanolamine, 2-(methylamino)ethanol, 2-(ethylamino)ethanol, 2-(propylamino)ethanol, 2-(butylamino)ethanol, and diisopropanolamine.

Examples of acrylates that can be used in this invention include methyl acrylate, vinyl acrylate, methyl methacrylate, ethyl acrylate, ethyl crotonate, allyl methacrylate, tert-butyl acrylate, isobutyl acrylate, methyl-2-hexenoate, butyl acrylate, isobutyl acrylate, ethyl sorbate, isopentyl acrylate, tert-butyl methacrylate, butyl methacrylate, isobutyl methacrylate, methyl-2-octenoate, hexyl acrylate, methyl-2-nonenoate, ethyl-2-octenoate, hexyl-2-butenoate, methyl-2-decenoate, isooctyl acrylate, 2-ethylhexyl acrylate, ethyl-2-methyl-2-nonenoate, 2-ethylhexyl 2-methylacrylate, decyl acrylate, decyl 2-methylacrylate, 8-methylnonyl 2-methylacrylate, and dodecyl acrylate. The preferred acrylates in this invention are methyl acrylate, butyl acrylate, and dodecyl acrylate. Examples of maleates that can be used in this invention include dimethyl maleate, diethyl maleate, dipropyl maleate, dibutyl maleate, dihexyl maleate, dioctyl maleate, and bis(2-ethylhexyl)maleate. The preferred maleates are dibutyl maleate and bis(2-ethylhexyl)ethylhexyl) maleate.

Borate Esters

The borate esters used in this invention are the reaction products of the hydroxylalkyldithiocarbamate esters described above with boric acid at a temperature between 80 and 150° C., as shown in Scheme II. Alcohols can also be added to the reaction to produce a mixed product that contains both alkoxy and hydroxyalkyldithiocarbamate ester on the boron. (Scheme III) The hydroxyalkyldithiocarbamate ester and boric acid are added to a reaction flask, and then the mixture is heated to a temperature between 80 and 150° C. The mixture is heated until the expected amount of water is liberated from the reaction, usually three equivalents per boron. The material is then filtered, revealing the product.

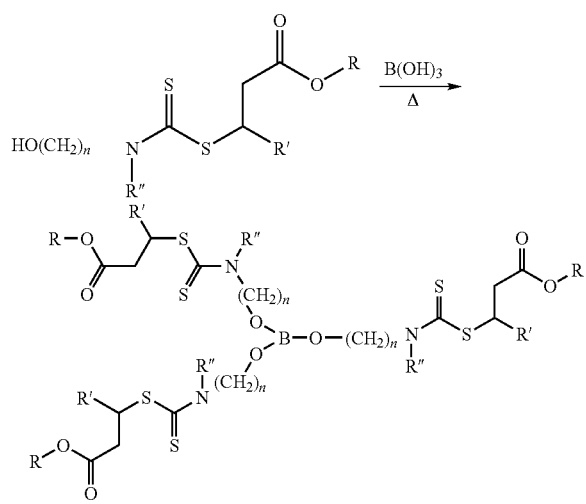

Scheme II

R = alkyl, $C_1$ to $C_{25}$
R' = H, $CO_2R$
R" = $(CH_2)_mOH$, m = 1 to 8: or alkyl, $C_1$ to $C_{25}$
n = 1 to 8

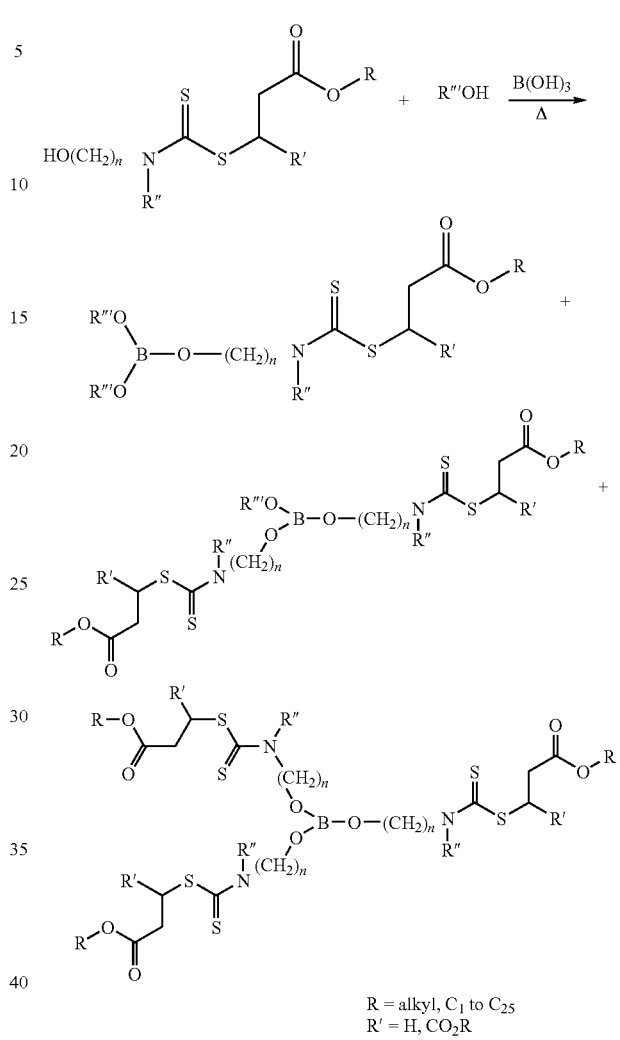

Scheme III

R = alkyl, $C_1$ to $C_{25}$
R' = H, $CO_2R$
R" = $(CH_2)_mOH$, m = 1 to 8: or alkyl, $C_1$ to $C_{25}$
R''' = alkyl, $C_1$ to $C_{25}$
n = 1 to 8

Examples of alcohols that can be used in this invention include methanol, ethanol, propanol, isopropanol, butanol, isobutanol, tertbutanol, basically all chain lengths can be used. Fatty alcohol mixtures such as those marketed under the trade name Alfol® by Sasol North America, and those marketed by The Procter and Gamble Company can also be used. These mixtures range from $C_8$ to $C_{18}$ in alkyl chain length. The preferred alcohols used are the long-chain fatty alcohol mixtures, 2-ethylhexanol, and butanol.

Lubricant Compositions

The borate ester compositions provide excellent antiwear and extreme pressure properties when incorporated into a lubricating formulation. The borate ester compositions of the invention may be present in a lubricating formulation at from about 0.01-10 mass %, preferably about 0.1-5 mass %, and more preferably about 1-3 mass %.

For ease of incorporation into the lubricating formulation, the reaction product can be dissolved in or diluted with a diluent compatible with the lubricating formulation. The base oil of the lubricants may be selected from naphthenic, aromatic, paraffinic, mineral and synthetic oils. The synthetic oils may be selected from, among others, alkylene polymers, polysiloxanes, carboxylic acid esters and polyglycol ethers.

The lubricating compositions may contain the necessary ingredients to formulate the composition, as for example emulsifiers, dispersants and viscosity improvers. Greases may be prepared by adding thickeners, as for example, salts and complexes of fatty acids, polyurea compounds, clays and quaternary ammonium bentonite complexes.

Depending on the intended use of the lubricant, other functional additives may be added to enhance a particular property of the lubricant. The lubricating compositions may further contain extreme pressure agents, metal passivators, rust inhibitors, dispersants and other known antioxidants, antifriction, and antiwear agents. Examples of extreme pressure agents include sulfurized olefins, 2,5-dimercaptothiadiazole derivatives, metal dithiocarbamate complexes, metal dithiophosphate complexes, and organic dithiocarbamate esters. Examples of common antioxidants include alkylated diphenyl amines, hindered phenols, polyphenyl thioethers, alkylated napthylamines, alkylated dinapthylamines, zinc dithiophosphates, and zinc dithiocarbamates. Examples of antifriction additives include molybdenum dithiocarbamates, molybdate esters, molybdenum amine complexes, and molybdenum dithiophosphates.

Examples of friction modifiers include fatty amines, mono- and diethoxylated amines, carboxylic acids, amides, imides, alcohols, phenols, esters, thiols, sulfonic acids, phosphates, phosphates.

EXAMPLES

Example 1

To diethanolamine (36.95 g, 0.35 moles) and dibutylmaleate (81.03 g, 0.35 moles) was added $CS_2$ (28.04 g, 0.37 moles) dropwise over a 15 minute period. The mixture was then heated to 80° C. for 6 hours followed by removal of the excess $CS_2$ to give 141.04 g (96.5% yield) of a yellow liquid.

Example 2

To dibutylmaleate (136.97 g, 0.60 moles) and 2-(ethylamino)ethanol (53.48 g, 0.60 moles) was added $CS_2$ (60.00 g, 0.79 moles) over a 10 minute period. The mixture was then heated at 70° C. for 6.5 hours to give 222.46 g (94% yield) of a thick yellow liquid after the excess $CS_2$ was distilled off.

Example 3

To the product of Example 2 (68.1 g, 0.173 moles) was added 2-ethylhexanol, (45.07 g, 0.346 moles) boric acid, (10.70 g, 0.173 moles) and 80 g of toluene. The mixture was then heated at 100-125° C. for 6 hours. 9.3 g of water was distilled off as well as the toluene, which gave 110.52 g of product following filtration and analyzing as having 1.7% B and 7.5% S by weight.

Example 4

To the product of Example 2 (78.53 g, 0.20 moles) was added boric acid, (4.00 g, 0.061 moles) and 80 g of toluene. The mixture was then heated at 100-125° C. for 6 hours. 3.6 g of water was distilled off as well as the toluene, which gave 80.53 g of product following filtration.

Example 5

To 2-ethylhexyl acrylate (67.10 g, 0.36 moles) and 2-(ethylamino)ethanol (32.46 g, 0.36 moles) was added $CS_2$ (32.00 g, 0.42 moles) over a 10 minute period. The mixture was then heated at 70° C. for 7 hours to give 113.43 g (90% yield) of a thick yellow liquid after the excess $CS_2$ was distilled off.

Example 6

To the reaction product of example 5 (57.51 g, 0.17 moles) was added Exxal® 13 (68.15 g), boric acid, (10.21 g, 0.17 moles) and 60 g of toluene. The mixture was then heated at 110° C. for 4 hours. 3.6 g of water was distilled off as well as the toluene, which gave 80.53 g of product following filtration.

Example 7

To 2-ethylaminoethanol (24.00 g, 0.27 moles) and Di-2-ethylhexyl maleate (95.19 g, 0.27 moles) was added carbon disulfide (50 g, 0.65 moles) dropwise with stirring. The mixture was then heated at 50° C. for 2 hours, then 70° C. for 3 hours. The reaction was then cooled to give 135.84 g of product following distillation of the excess carbon disulfide.

Example 8

To the reaction product of Example 7 (77.49 g, 0.15 moles) was added Exxal® 13 (72.00 g), boric acid, (9.00 g, 0.15 moles) and 50 g of toluene. The mixture was then heated at 110° C. for 6 hours. 7.86 g of water was distilled off as well as the toluene, which gave 134.5 g of product following filtration and analyzing as 1.0% B and 6.2% S by weight.

Example 9

To 2-(butylamino)ethanol (53.50 g, 0.46 moles) and Di-2-ethylhexyl maleate (155.45 g, 0.46 moles) was added carbon disulfide (36.00 g, 0.47 moles) dropwise with stirring. The mixture was then heated at 50° C. for 2 hours, then 70° C. for 2 hours. The reaction was then cooled to give 240.80 g of product following distillation of the excess carbon disulfide.

Example 10

To the reaction product of Example 9 (67.25 g, 0.13 moles) was added boric acid, (2.47 g, 0.04 moles) and 150 g of toluene. The mixture was then heated at 110° C. for 6 hours. 2.11 g of water was distilled off as well as the toluene, which gave 72.71 g of product following filtration and analyzing as having 1.0% B by weight.

Example 11

To diethanolamine (35.51 g, 0.34 moles), di-2-ethylhexyl maleate (115.00 g, 0.46 moles), and 70 g of isopropanol was added carbon disulfide (40.00 g, 0.53 moles) dropwise with stirring. The mixture was then heated at 50° C. for 2 hours, then 75-80° C. for 2 hours. The reaction was then cooled to give 174.17 g of product following distillation of the excess carbon disulfide and isopropanol.

Example 12

To diethanolamine (34.14 g, 0.32 moles), lauryl acrylate (90%) (86.73 g, 0.32 moles), and 70 g of isopropanol was added carbon disulfide (40.00 g, 0.53 moles) dropwise with stirring. The mixture was then heated at 50° C. for 2 hours, then 75-80° C. for 2 hours. The reaction was then cooled to give 136.51 g of product following distillation of the excess carbon disulfide and isopropanol.

Example 13

To the reaction product of Example 12 (51.06 g, 0. moles) was added boric acid, (3.20 g, 0.04 moles). The mixture was then heated at 110° C. for 6 hours under aspirator vacuum. 2.80 g of water was distilled off, and 72.71 g of product was recovered following filtration and analyzing as having 1.0% B and 12.1% S by weight.

Example 14

To 2-(butylamino)ethanol (29.10 g, 0.25 moles), lauryl acrylate (90%) (66.06 g, 0.25 moles), and 70 g of isopropanol was added carbon disulfide (21.00 g, 0.28 moles) dropwise with stirring. The mixture was then heated at 50° C. for 2 hours, then 75-80° C. for 2 hours. The reaction was then cooled to give 11.02 g of product following distillation of the excess carbon disulfide and isopropanol.

Example 15

To the reaction product of Example 16 (32.04 g, 0.07 moles) was added boric acid (4.20 g, 0.071 moles) and 75 g of toluene. The mixture was then heated at 110° C. for 6 hours under aspirator vacuum. 1.1 mL of water was distilled off as well as the toluene, which gave 33.14 g of product following filtration.

Example 16

Falex Pin and Vee Block Tests

A laboratory test was conducted by using the original Falex machine to simulate the valve train wear of an automobile engine. The V-blocks and pin were washed in mineral spirits with an ultrasonic cleaner, rinsed with acetone, air dried and weighed. The test sample (60 g) was placed into the oil cup. The motor was switched on and the loading arm was placed on the ratchet wheel. Upon reaching the reference load of 227 Kg, the ratchet wheel was disengaged and the load was maintained constant for 1 or 3.5 hours. Thereafter, the motor was switched off. The V-blocks and pin were washed, dried and weighed. The weight loss, a measure of wear, was recorded and compiled in Table I.

The test samples were prepared by adding the borate ester compound to a base oil, Uninap® SD 100 (manufactured by Unisource Energy, Inc.). Boron content was determined by Atomic Absorption techniques prior to dilution. The results are listed in Table 1.

TABLE 1

| | Mass Percent | | | | | | | |
|---|---|---|---|---|---|---|---|---|
| Example 3 Product | 1 | | | | | | | |
| Example 8 Product | | 1 | 1.63 | | | | | |
| Example 10 Product | | | | 2 | | | | |
| Example 13 Product | | | | | 1 | | | |
| Lubrizol Z 1395 * | | | | | | 1.5 | 2.0 | 5 |
| Uninap 100 SD | 99 | 99 | 98.37 | 98 | 99 | 98.5 | 98.0 | 95 |
| ppm B | ~170 | ~100 | ~163 | ~100 | ~100 | 0 | 0 | 0 |
| % P | 0 | 0 | 0 | 0 | 0 | 0.14 | 0.19 | 0.47 |
| Falex Pin & Vee Block 227 Kg for 60 minutes | | | | | | | | |
| Total Mass Loss (mg) | 12.7 | 7.9 | | 50.8 | | 44.8 | 221 | 396 |
| Actual Test Time (min.) | 60 | 60 | | 60 | | 13 sec. | 15 sec. | 47 |
| Falex Pin & Vee Block 227 Kg for 210 minutes | | | | | | | | |
| Total Mass Loss (mg) | | | 3.1 | | | | | |
| Actual Test Time (min.) | | | 210 | | | | | |
| Falex Pin & Vee Block 227 Kg for 180 minutes | | | | | | | | |
| Total Mass Loss (mg) | | | | | 30.9 | | | |
| Actual Test Time (min.) | | | | | 180 | | | |

* Lubrizol Z 1395 is a zinc dithiophosphate manufactured by Lubrizol Corporation.

Example 17

4-Ball Weld and Wear Tests

The reaction products of Examples 12 and 15 were evaluated for their 4-Ball Weld and 4-Ball Wear properties in accordance with ASTM 2596 and ASTM 2266 respectively. An oil formulation with Exxon ISO 220 Blend (manufactured by Exxon-Mobil Corporation) was prepared with the reaction product of Example 12, and a grease formulation was prepared with Exxon-Mobil Lithium-12 hydroxystearate grease (manufactured by Exxon-Mobil Corporation). The results are listed in Table 2.

TABLE 2

| | Mass Percent | | | |
|---|---|---|---|---|
| Example 10 Product | 3 | | | |
| Example 13 Product | | 3 | | |
| Exxon ISO 220 Blend | 97 | | | 100 |
| EM Li-12OH Grease | | 97 | 100 | |
| ppm B | ~150 | ~300 | 0 | 0 |
| 4-Ball Weld Load, Kgf | 250 | 315 | 160 | 126 |
| 4-Ball Wear: | | | | |
| 1200 rpm, 75° C., 1 hour 40 Kgf, mm | 0.38 | 0.5 | 0.55/0.49 | 0.77 |
| 1800 rpm, 54o C., 1 hour 20 Kgf, mm | 0.54 | | | 0.87 |

The invention claimed is:

1. A composition comprising a hydroxyalkyldithiocarbamate ester according to the formula, wherein R=alkyl $C_1$ to $C_{25}$; R'=H or $CO_2R$; R"=$(CH_2)_m OH$, where m=1 to 8, or alkyl $C_1$ to $C_{25}$; n=1 to 8:

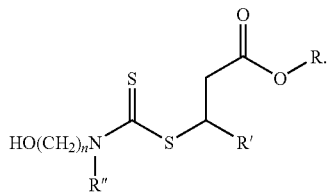

2. A hydroxyalkyldithiocarbamate ester being a reaction product of hydroxyalkylamine with $CS_2$, and an acrylate or maleate compound.

3. The hydroxyalkyldithiocarbamate ester according to claim 2, wherein the alkyl chain length between the hydroxyl and amine functionalities in the hydroxyalkylamine is between 1 and 8 carbon atoms.

4. The hydroxyalkyldithiocarbamate ester according to claim 2, wherein the hydroxyalkylamine is an N-alkyl ethanolamine with the alkyl group containing between 1 and 25 carbon atoms.

5. The hydroxyalkyldithiocarbamate ester according to claim 2, wherein the hydroxyalkylamine is N-butylethanolamine or N-ethylethanolamine.

6. The hydroxyalkyldithiocarbamate ester according to claim 2, wherein the hydroxyalkylamine is diethanolamine.

7. The hydroxyalkyldithiocarbamate ester according to 2, wherein the acrylate or maleate used contains alkyl group(s) between 1 and 25 carbon atoms.

8. The hydroxyalkyldithiocarbamate ester according to 2, wherein the acrylate or maleate is chosen from the group consisting of dodecylacrylate, di-2-ethylhexylmaleate and dibutylmaleate.

* * * * *

UNITED STATES PATENT AND TRADEMARK OFFICE
CERTIFICATE OF CORRECTION

| | | |
|---|---|---|
| PATENT NO. | : 7,589,226 B2 | Page 1 of 1 |
| APPLICATION NO. | : 11/255730 | |
| DATED | : September 15, 2009 | |
| INVENTOR(S) | : Chase et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 813 days.

Signed and Sealed this

Twenty-first Day of September, 2010

David J. Kappos
*Director of the United States Patent and Trademark Office*